United States Patent [19]
Kelley et al.

[11] Patent Number: 5,104,870
[45] Date of Patent: Apr. 14, 1992

[54] HETEROCYCLIC PHARMACEUTICAL COMPOUNDS AND USE

[75] Inventors: James L. Kelley; David L. Musso, both of Raleigh; Grady E. Boswell, Cary; Barrett R. Cooper, Durham, all of N.C.

[73] Assignee: Burroughs Wellcome Co., Research Triangle Park, N.C.

[21] Appl. No.: 680,637

[22] Filed: Apr. 2, 1991

Related U.S. Application Data

[63] Continuation of Ser. No. 605,890, Oct. 30, 1990, abandoned.

[30] Foreign Application Priority Data

Oct. 31, 1989 [GB] United Kingdom ............... 8924528

[51] Int. Cl.$^5$ ................ A61K 31/535; C07D 265/32
[52] U.S. Cl. ................................ 514/230.8; 544/173
[58] Field of Search ...................... 544/173; 514/230.8

[56] References Cited

U.S. PATENT DOCUMENTS

| | | | |
|---|---|---|---|
| 3,117,967 | 1/1964 | Anderson et al. | 544/173 |
| 4,576,944 | 3/1986 | Lafon | 544/173 |

FOREIGN PATENT DOCUMENTS

0139590A3  5/1985  European Pat. Off. .

OTHER PUBLICATIONS

European Patent Application, 170,430, 2-1986.

*Primary Examiner*—Robert W. Ramsuer
*Attorney, Agent, or Firm*—Donald Brown; Hannah O. Green; Lawrence A. Nielsen

[57] ABSTRACT

Novel (2S, 3S, 5R) morpholinols of formula (I)

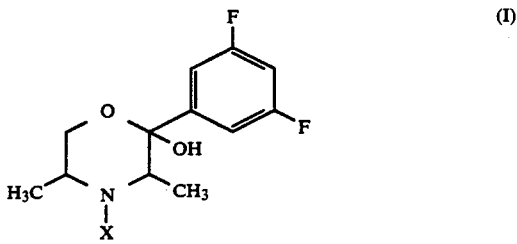

together with the (+ −)-(2R*,3R*,5S*) racemates thereof, and their salts,
wherein
X is hydrogen, alkyl of 1 to 6 carbon atoms, cycloalkyl of 3 to 6 carbon atoms or a group —CH$_2$—X$^1$ where X$^1$ is cycloalkyl of 3 to 6 carbon atoms.

The compounds have a variety of uses in human medicine, in particular in the treatment of mental disorders such as depression.

33 Claims, No Drawings

HETEROCYCLIC PHARMACEUTICAL COMPOUNDS AND USE

This is a continuation of copending application(s) Ser. No. 07/605,890 filed on Oct. 30, 1990 now abandoned.

The present invention relates to novel morpholinols useful in medicine, to processes for preparing them, to pharmaceutical formulations containing them and their preparation, to the use of the compounds in medicine and to novel chemical intermediates therefor and the preparation thereof.

Patent publication EP.A.0 170 430 discloses the compounds represented by the formula

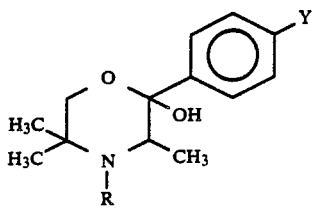

wherein Y is hydrogen or fluorine and R is hydrogen or alkyl ($C_{1-4}$). and salts thereof, and their antidepressant activity as demonstrated by widely accepted techniques used in the art of pharmacology for determining antidepressant activity, for example, the tetrabenazine, induced sedation test in rodents.

There are now provided the (2S,3S,5R) morpholinols of formula (I)

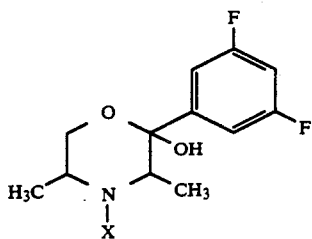

together with the (+-).(2R*.3R*,5S*) racemates thereof. and salts thereof, which have surprisingly also been found to exhibit antidepressant activity and to be markedly more potent, in the said tetrabenazine test, than the compounds specifically identified in the said EP.A publication.

Advantageously, in the therapeutic dose range, these novel morpholinols and their salts do not produce any significant degree of locomotor stimulation and are essentially free from proconvulsant activity.

In formula (I).

X is hydrogen, alkyl of 1 to 6 carbon atoms, cycloalkyl of 3 to 6 carbon atoms or a group —$CH_2$—$X^1$ where $X^1$ is cycloalkyl of 3 to 6 carbon atoms.

When X is alkyl of 3 to 6 carbon atoms the said group may be linear or branched.

Unless the context clearly indicates otherwise, as used herein the term "compound(s) of formula (I)" generically denotes the above recited (2S,3S,5R) compounds and (+-).(2R*,3R*,5S*) racemates.

The present invention should be understood to include a said (2S,3S, 5R) compound, or salt thereof, substantially free from the (2R,3R, 5S)-enantiomorph., as used herein, "substantially free" means that the latter is present in an amount of not more than 5% (w/w) of the former.

Preferred compounds of formula (I) are those wherein X is hydrogen or alkyl of 1 to 6, in particular 1 to 4 and most particularly 1 or 2. carbon atoms, and salts thereof.

Especially preferred are the (2S,3S,5R) compound of formula (Ia)

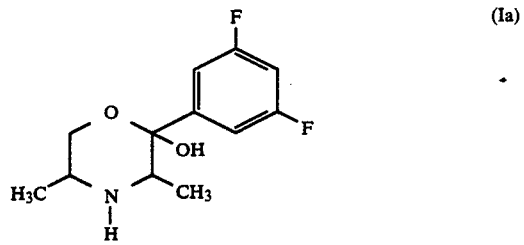

chemically named (2S,3S,5R)-2-(3,5-difluorophenyl)-3,5-dimethyl-2-morpholinol, and salts thereof, and the (+-)-(2R*,3R*,5S*) racemate, chemically named (+-).(2R*.3R*.5S*).2.(3.5.difluorophenyl).3 5.-dimethyl- 2-morpholinol, and salts thereof.

As will be appreciated, structural formulae (I) and (Ia) are merely two-dimensional representations of the respective compounds and do not denote the indicated stereochemistry.

The compounds of formula (I) and their salts may be prepared by those methods known in the art for the synthesis of compounds of analogous structure and in this regard reference is made, by way of illustration only, to the following standard texts:

(i) "*Protective Groups in Organic Chemistry*" ed. J. F. W McOmie. Plenum Press (1973), ISBN 0.306.30717.0;

(ii) "*Comoendium of Organic Synthetic Methods*" ed. I. T Harrison and S. Harrison. Wiley. Interscience, Vol. I (1971) ISBN 0.471.35550.X. Vol. II (1974) ISBN 0.471.35551.8 and Vol. III (ed L. S. Hegedus and L. Wade) (1977) ISBN 0.471.36752 4; and (iii) Rodd's "*Chemistry of Carbon Compounds*" second edition. Elsevier Publishing Company.

1. One method comprises reaction of an alcohol (II) having the appropriate chirality wherein X is as defined in formula (I). with a ketone (III) wherein L is a leaving atom or group such as conveniently be conducted in a solvent such as acetonitrile. dichloromethane, ethanol or methanol and at a temperature in the range 20° to 40° C.

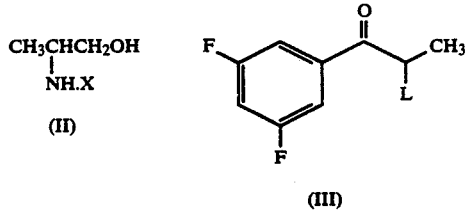

It will be appreciated that use in this manner of a racemic (compound (II)) affords the (+-)-(2R*,3R*,5S*) racemate of formula (I) while an (R)-alcohol selectively provides the (2S,3S,5R) compound.

2. The compounds wherein X is other than hydrogen may also be prepared by reaction of the corresponding compound of formula (I) wherein X is hydrogen with a reagent (IV)

$$X^2—L^1 \qquad (IV)$$

where $X^2$ is a group X as defined in formula (I). other than hydrogen, and $L^1$ is a leaving atom or group such as halo (for example, chloro, bromo or iodo). The reaction may conveniently be conducted in a solvent such as acetonitrile, dichloromethane ethanol or methanol and at a temperature in the range 20° to 100° C.

3. The (2S,3A,5R) compounds can also be obtained by resolution of the corresponding (+-)-(2R*,3R*,5S*) racemate This may be accomplished in a conventional manner, by forming the diastereomeric salts of the latter with an optically active acid for example (+) or (.).tartaric acid or (+) or (-)-dibenzoyl-L. or D-tartaric acid monohydrate, in an appropriate solvent, for example aqueous ethanol, followed by recrystallization of the appropriate (diastereomeric) salt and isolation of the morpholinol free base.

The compounds of formula (I) and their pharmaceutically acceptable salts may be used in the treatment of depression in human beings identified as being depressed, the treatment comprising the administration of an antidepressant effective, non-toxic amount (dose). preferably in a unit dosage form of a compound of formula (1) or a pharmaceutically acceptable salt thereof.

Depression states in the treatment of which the said compounds and salts are particularly useful are those classified as *affective disorders* in the *Diagnostic and Statistical Manual of Mental Disorders.* Third Edition Revised—American Psychiatric Association. Washington D.C. (1987) (DSM.III.R), including the mood disorders (DSM.III.R 296.2X to 296.6X), other specific affective disorders (301.13 and 300.40) and bipolar and depressive disorders not otherwise specified (296.70 and 311.00).

Other uses in human therapy for these compounds and salts include the treatment of the following conditions. the classifications (where indicated) being those adopted in DSM.III.R:

anxiety disorders, including phobic neuroses (300 00 300.21, 300.22, 300.23 and 300.29). anxiety neuroses (300.01, 300.02 and 300.30) and post-traumatic stress disorder (309.89)

attention deficit disorders (314.00 and 314.01)

eating disorders, including anorexia nervosa (307 10) and bulimia (307.51)

personality disorders, including borderline personality disorder (301 83)

sexual dysfunctions, including hypoactive sexual desire disorder (302.71), female sexual arousal disorder or male erectile disorder (302.72). inhibited female orgasm (302.73), inhibited male orgasm (302.74). premature ejaculation (302.75), dyspareunia (302.76), vaginismus (306.51) and sexual dysfunction not otherwise specified (302.70)

headaches including migraine, muscle contraction and mixed (i.e. combination of migraine and muscle contraction) headaches narcolepsy-cataolexy syndrome, a condition characterized by excessive sleepiness (narcolepsy) often taking the form of sleep attacks, episodes of a seemingly irresistible need to sleep usually lasting for about fifteen minutes or less, together with brief (often lasting less than a minute) periods of loss of muscle tone (cataplexy) occurring in association with the expression of emotion.

The compounds and salts may further be used in human medicine:

to alleviate symptoms of withdrawal consequent upon the cessation of illicit drug abuse to potentiate the analgesia induced by morphine or a like opiate analgesic, for example in the care and treatment of terminally-ill cancer patients to prevent functional impairment and drowsiness following administration of a drowsiness-inducing benzodiazepine tranquillizer; suitable indications for concomitant administration of a said compound or salt and such a benzodiazepine include a) treatment of mixed anxiety and depression in situations where functional impairment or drowsiness is undesirable, and b) treatment of anxiety in situations where functional impairment or drowsiness is undesirable to prevent memory loss following administration of a benzodiazepine tranquillizer to restore mental functioning acutely impaired consequent upon ethanol ingestion to suppress prolactin release or secretion, for example in the suppression of lactation post partum or in the treatment of galactorrhoea, hyperprolactinaemia, amenorrhoea resulting from hyperprolactinaemia and prolactin-sensitive mammary cancer to treat memory loss and other memory deficits associated with benign senility.

For each of the foregoing indications, the preferred dosage for parenteral (including subcutaneous, intramuscular and intravenous) administration of a compound of formula (I) or salt thereof (estimated as the base) is in the range 0.05 mg/kg to 10 mg/kg of body weight per day, the most preferred dosage being in the range 0.1 mg/kg to 5 mg/kg of body weight per day. For the oral, rectal, topical (including buccal and sublingual) or transdermal route of administration, the preferred dosage of a compound of formula (I) or salt thereof (estimated as the base) is in the range 0.05 mg/kg to 20 mg/kg of body weight per day while the most preferred dosage is in the range 0.1 mg/kg to 10 mg/kg of body weight per day.

As will be understood, the precise dosage will depend upon a number of clinical factors, for example, the age of the recipient and the condition in question and its severity.

The preferred unit dosage of a compound of formula (I) or salt thereof (estimated as the base) for parenteral (including subcutaneous. intramuscular and intravenous), oral, rectal or topical (including buccal and sublingual) administration is in the range 1 mg to 200 mg with the more preferred unit dosage being in the range 5 mg to 150 mg. and the most preferred unit dosage being in the range 10 mg to 100 mg.

All the above doses are expressed in terms of the weight of the base but a compound of formula (I) is preferably administered in the form of a pharmaceutically acceptable salt thereof.

A compound of formula (I) or salt thereof is preferably administered four times daily although this may vary according to the patient being treated, and at the physician's discretion.

While it is possible for the active compound, i.e.. compound of formula (I) or pharmaceutically acceptable salt thereof, to be administered alone as the raw chemical, it is preferable to present it as a pharmaceutical formulation comprising a compound of formula (I) (or a pharmaceutically acceptable salt thereof) together with an acceptable carrier therefor.

The carrier should be acceptable in the sense of being compatible with the other ingredients of the formulation and not deleterious to the recipient thereof.

Conveniently the active compound comprises from 5 to 95% by weight of the formulation.

The formulations include those suitable for oral, rectal, topical (including buccal and sublingual). parenteral (including subcutaneous. intramuscular and intravenous) or transdermal administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, shaping the product.

Formulations of the present invention suitable for oral administration may be presented as discrete units such as capsules cachets, tablets or lozenges, each containing a predetermined amount of the active compound; as a powder or granules including microencapsulated or time-release forms., or as a suspension or solution in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, the active compound being in a free-flowing form such as a powder or granules optionally mixed with a binder, disintegrant, lubricant, inert diluent, surface active agent or dispersing agent. Molded tablets comprising a mixture of the powered active compound with any suitable carrier may be made by molding in a suitable machine.

Formulations suitable for rectal administration may be presented as a suppository with a conventional carrier such as cocoa butter. hydrogenated fats or hydrogenated fatty carboxylic acids Formulations suitable for topical administration in the mouth, for example buccally or sublingually, include lozenges comprising the active compound in a flavored basis such as sucrose and acacia or tragacanth, and pastilles comprising the active compound in a basis such as gelatin and glycerin or sucrose and acacia.

Formulations suitable for parenteral administration conveniently comprise a sterile aqueous preparation of the active compound which is preferably isotonic with the blood of the intended recipient. The formulations may be presented in unit-dose or multi-dose containers for example sealed ampoules and vials, and may be stored in a freeze-dried state requiring only the addition of the sterile liquid carrier, for example water, just prior to use. As an alternative possibility, the active compound may be presented in the form of liposomes.

Formulations suitable for transdermal administration may be presented as discrete patches adapted to remain in intimate contact with the epidermis of the recipient for a prolonged period of time. Such patches suitably contain the active compound as an optionally buffered, aqueous solution of for example. 0.1 to 0.2M concentration with respect to the said compound. As one particular possibility, the active compound may be delivered from the patch by iontophoresis as generally described in *Pharmaceutical Research*. 3/6, 318 (1986).

In addition to the aforementioned ingredients, the formulations of this invention may further include one or more accessory ingredient(s) selected as appropriate from diluents, buffers, flavoring agents, binders. disintegrants, surface active agents, thickeners, lubricants. preservatives (including antioxidants) and the like.

When used in medicine, the salts of a compound of formula (I) should be pharmaceutically acceptable, but pharmaceutically unacceptable salts may conveniently be used to prepare the corresponding free base or pharmaceutically acceptable salts thereof and are included within the scope of this invention.

Such pharmaceutically acceptable salts include, but are not limited to, those prepared from the following acids: hydrochloric. hydrobromic, sulfuric, nitric, phosphoric, salicylic, p-toluenesulfonic, tartaric, citric, methanesulfonic, maleic, formic. malonic, succinic, isethionic, lactobionic, naphthalene.2-sulfonic. sulfamic, ethanesulfonic and benzenesulfonic.

The NMR spectra and other physicochemical data are consistent with the compounds of formulae (I) and (Ia) having the indicated cyclic (i e morpholinol) structure. It is however possible that under certain, as yet undefined, conditions they exist at least in part as the corresponding acyclic tautomers represented two-dimensionally by the formula

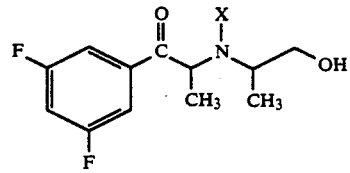

Wherever used herein, formulae (I) and (Ia) should thus be understood to embrace the said tautomeric forms.

The following Examples are provided by way of illustration of the present invention and should not be construed as a limitation thereof.

EXAMPLE 1

(+-)-(2R*,3R*,5S*)-2-(3,5-Difluorophenyl)-3,5-dimethyl-2-morpholinol hydrochloride To a solution of 3,5-difluorobenzonitrile (Aldrich Chemical Co . Milwaukee. WI 53233)(50.0 g. 0.36 mole) in 500 mL of diethyl ether at 0° C. was added dropwise a solution of ethylmagnesium bromide (135 mL of a 3.OM solution 0.41 mole) in diethyl ether. The reaction mixture was refluxed for 3 hr. then chilled in an ice bath and hydrolyzed with 100 mL of 6N aqueous hydrogen chloride. The mixture was heated on a steam bath for 0.5 hr. The pH was adjusted to acid (litmus) and two phases were separated by extraction of the aqueous phase with diethyl ether. The combined extracts were dried (sodium sulfate) and concentrated in vacuo to give 61.3 g (91% of theory) of crude 3',5'-difluoropropiophenone.

A solution of dioxane dibromide, prepared by the dropwise addition of bromine (52.7 g. 0.33 mole) to 500 mL of dioxane. was added dropwise to a solution of 3',5'-difluoropropiophenone (56.0 g. 0.33 mole) in 500 mL of dioxane. After stirring at room temperature overnight the reaction mixture was poured into 2.5 L of water The aqueous solution
was extracted with dichloromethane. The extracts were dried (sodium sulfate). and concentrated in vacuo to give crude 2.bromo.3', 5'-difluoropropiophenone. After distillation on a Kugelrohr a a boiling point of 60°-62° C. and 0.3 mm Hg, the product 2.bromo.3',5' -difluoropropiophenone had a refractive index $\eta^{21.1°} = 1.5273$.

Elemental Analysis: Calcd. for $C_9H_7BrF_2O$ (m.w. 249.06): C, 43.40%; H, 2.83%. Found: C, 43.53%; H, 2.88%.

NMR-$^1$H: (DMSO-d$_6$) $\delta$1.91 (d, 3H. CH$_3$)5.14 (q. 1H, CH), 7.02-7 55 (aromatic H's).

To a solution of 2-bromo.3',5'-difluoropropiophenone (25 0 g. 0.10 mole) in acetonitrile (100 mL) was added a solution of dl-2-amino-1-propanol (Aldrich Chemical Co . Milwaukee. WI 53233) (8.3 g. 0.11 mole) and 2.6.lutidine (15 0 g. 0 14 mole) in acetonitrile (100 mL). After stirring for six days at room temperature, the resulting solid was filtered, washed with diethyl ether and dried to give (+-)-(2R*,3R*,5S*),2-(3.5.difluorophenyl) 3,5-dimethyl-2-morpholinol hydrobromide. Recrystallization of a sample from ethanol-diethyl ether mixtures gave a white solid M P 228°-229° C. dec.

Elemental Analysis: Calcd. for $C_{12}H_{16}BrF_2NO_2$ (m.w. 324 16): C. 44.46%; H. 4.98%; N. 4.32%. Found: C. 44.35%; H, 5.00%; N, 4 30%.

A solution of (+.).(2R*,3R*, 5S*)-2-(3,5-difluorophenyl)-3,5-dimethyl-2-morpholinol hydrobromide (8.0 g, 0.02 mole) in water was basified with 50% aqueous sodium hydroxide and extracted with diethyl ether. The diethyl ether solution was dried (potassium carbonate) and concentrated under reduced pressure to yield the free base M.P. 140°-142° C. after recrystallization from hexane. The free base was dissolved in diethyl ether and treated with ethereal hydrogen chloride. The hydrochloride salt was recrystallized from ethanol-diethyl ether mixtures to give (+-)-(2R*,3R*,5S*)-2-(3,5-difluorophenyl)-3,5-dimethyl -2-morpholinol hydrochloride as a white solid. M.P. 228°-229° C. dec.

Elemental Analysis: Calcd. for $C_{12}H_{16}ClF_2NO_2$ (m.w. 279 71) C. 51.52%., H, 5.77%; N. 5.01%. Found: C. 51.46%; H, 5.82%; N. 5.00%.

NMR-$^1$H: (DMSO-d$_6$) $\delta$0.96 (d, 3H, CH$_3$). 1.21 (d. 3H. CH$_3$). 3.44 (broad multiplet, 2H, CH), 3.85 (multiplet, 2H. CH$_2$), 7.17-7.32 (aromatic H's), 7.63 (d. 1H. OH). 8.77 and 10.33 (broad, 2H. HCl and NH).

EXAMPLE 2

(2S,3S,5R).2.(3,5.Difluorophenyl).3.5.dimethyl-2-morpholinol hydrochloride

To 3',5'-difluoropropiophenone (56.0 g. 0 33 mole) was added a solution of dioxane dibromide (81.8 g. 0.33 mole) in dioxane (500 ml) The reaction mixture was worked up as in Example 1 to yield crude 2-bromo-3',5'-difluoropropiophenone (83.9 g).

To a solution of 2-bromo-3',5'-difluoropropiophenone (22 4 g. 0.09 mole) in acetonitrile (60 ml) was added a solution of R-(-)-2-amino-1-propanol (Aldrich Chemical Co.. Milwaukee. WI 53233) (7.5 g, 0.10 mole) and 2.6.lutidine (11.8 g. 0.11 mole) in acetonitrile (100 ml). The reaction mixture was worked up as in Example 1 to give (2S,3S,5R)-2-(3,5.difluorophenyl)-3,5-dimethyl-2-morpholinol hydrobromide Recrystallization of a sample from ethanol-diethyl ether mixtures gave a white solid. M.P. 240°-241° C. dec.

Elemental Analysis: Calcd. for $C_{12}H_{16}BrF_2NO_2$ (m.w. 324 16): C 44.46%; H, 4.98%; N. 4.32%. Found: C, 44.45%; H. 5.00%; N. 4 24% $[\alpha]_D^{20} = +34.6°$ (95% ethanol. c =0.687).

A solution of (2S,3S,5R)-2-(3,5-difluorophenyl)-3,5-dimethyl-2-morpholinol hydrobromide (7.5 g 0.023 mole) in water was basified with 40% aqueous sodium hydroxide and extracted with diethyl ether The diethyl ether layers were combined, washed with brine, dried (potassium carbonate) and concentrated under reduced pressure to yield the free base. M.P. 113°-115° C. after recrystallization from hexane $[\alpha]_D^{20} = +65.3°$ (c=0.658. 95% ethanol).

NMR$^1$H (DMSO-d$_6$) $\delta$0.68 (d, 3H, CH$_3$) 0.93 (d. 3H. CH$_3$). 1 84 (broad. 1H, NH), 2.82 (br q. 1H, CH). 2.97 (br m. 1H. CH). 3.49 (m. 2H. CH$_2$). 6.46 (s. 1H. OH). 7.10-7.20 (aromatic H's).

This free base was dissolved in diethyl ether and treated with etherial hydrogen chloride. The hydrochloride salt was recrystallized from ethanol-diethyl ether mixtures to give (2S,3S,5S,2-(3,5- difluorophenyl)-3,5-dimethyl-2-morpholinol hydrochloride as a white solid. M.P. 255°-257° C.

Elemental Analysis: Calcd. for $C_{12}H_{16}ClF_2NO_2$ (MW 279.71): C, 51.52%; H. 5 77%; N. 5.01%. Found: C, 51.62%; H, 5.76%; N. 4.98%. $[\alpha]_D^{20} = +42.1.*$ (95% ethanol. c =0 687).

NMR-$^1$H: (DMSO.d$_6$) $\delta$0.97 (d. 3H. CH$_3$). 1.20 (d. 3H. CH$_3$). 3.49 (broad multiplet, 2H, CH), 3 83 (sharp multiplet. 2H, CH2). 7.17-7.34 (aromatic H's). 7.62 (s. 1H. OH). 8.75 and 10.10 (broad. 2H, HCl and NH).

EXAMPLE 3

(2S,3S,5R)-2-(3.5.Difluorophenyl)-3,4,5,trimethyl-2-morpholinol hydrochloride, one-quarter hydrate To a chilled suspension of (2S,3S,5R)-2-(3,5-difluorophenyl)-3 5-dimethyl-2-morpholinol hydrochloride (Example 2) (10.0 g, 0.036 mole) in a mixture of water (100 ml) and diethyl ether (100 ml) was added sodium hydroxide as a 50% aqueous solution until the mixture was basic. The layers were separated and the aqueous layer extracted with diethyl ether. The combined extracts were dried (potassium carbonate). filtered and concentrated under reduced pressure to give (2S,3S,5R)-2-(3,5-difluorophenyl)-3,5-dimethyl-2-morpholinol (8 7g) A mixture of this base (8.7g. 0.036 mole) and methyl iodide (7.7g. 0.054 mole) in acetonitrile (50ml) was placed in a Wheaton pressure bottle and warmed in a water bath on a steam bath for 48 h. Further methyl iodide (7.7g, 0.054 mole) was then added and the mixture warmed for an additional five days. The reaction mixture was then concentrated under reduced pressure and the residue partitioned between diethyl ether and sodium hydroxide (1N aq.). The ether phase was dried (sodium sulphate). filtered and concentrated under reduced pressure. The residue was purified by column chromatography on silica gel using ethyl acetate: ethanol (95:5) as eluent to give (2S,3S,5R)-2-(3,5-difluorophenyl)-3,4,5,trimethyl-2-morpholinol This was dissolved in diethyl ether and a solution of 1.0M hydrogen chloride in diethyl ether added. The resulting salt was filtered washed with diethyl ether and recrystallised from acetonitrile: diethyl ether mixtures to give the title compound as a white solid. M.P 212°-214° C. eff. $[\alpha]_D^{20} = +50.35°$ (c=0.727, 95% ethanol).

Elemental Analysis: Calcd. for $C_{13}H_{18}ClF_2NO_2$. ¼ $H_2O$ (m.w. 298 25): C, 52.35%; H, 6.25%; N. 4.70%; $H_2O$, 1.51%. Found: C. 52.48%; H. 6.24%; N. 4.71%; H20, 1.34%.

NMR[1]H: (DMSO.$d_6$/$D_2O$) δ1.01 (d, 3H, $CH_3$), 1.26 (d,3H, $CH_3$), 2.76 (s. 3H, $CH_3$). 3.55 (broad multiplet, 2H, CH). 3.90 (sharp multiplet 2H. $CH_2$), 7.19–7.30 (aromatic H's).

EXAMPLE 4

(+-)-(2R*,3R*,5S*)-2-(3,5-Difluorophenyl)-3,4,5,trimethyl-2-morpholinol hydrochloride This was prepared from (+-)-(2R*,3R*,5S*)-2-(3,5-difluorophenyl)-3,5-dimethyl-2-morpholinol hydrochloride (Example 1) using a procedure analogous to that of Example 3. The product was obtained as a white solid. M.P. 191°–193° C. eff.

Elemental Analysis. Calcd. for $C_{13}H_{18}ClF_2NO_2$ (m.w. 293.74): C. 53.15%; H. 6.18%; N. 4.77%. Found: C. 53.05%; H. 6.22%; N. 4.75%.

NMR-[1]H: (DMSO.$d_6$/$D_2O$) δ1.02 (d, 3H, $CH_3$), 1.27 (d, 3H, $CH_3$). 2.77 (s, 3H, $CH_3$). (broad multiplet is under HOD peak). 3 93 (sharp multiplet. 2H, $CH_2$), 7.20.–7.29 (aromatic H's).

EXAMPLE 5

(2S,3S,5R)-2-(3,5-Difluorophenyl)-4-ethyl-3,5-dimethyl-2-morpholinol hydrochloride, monohydrate This was prepared from (2S,3S,5R)-2-(3,5-difluorophenyl)-3,5-dimethyl -2-morpholinol hydrochloride (Example 2) by a procedure analogous to that of Example 3, using ethyl iodide in place of methyl iodide The product was obtained as a white solid. M.P 169°–172° C. eff. $[\alpha]_D^{20} = +46.36°$ (c =0.701, 95% ethanol).

Elemental Analysis: Calcd. for $C_{14}H_{20}ClF_2NO_2$ $H_2O$ (m.w. 325 78): C. 51.61%; H. 6.81%; N. 4 30%. Found: C. 51.61%; H. 6 82%; N. 4 30%

NMR-[1]H (DMSO.$d_6$) δ0.98 (d, 3H, $CH_3$), 1.14 (t, 3H, $CH_3$). 1 24 (d. 3H, $CH_3$), 3.24 (m. 2H. CH). 3.60 (broad triplet. 1H. CH). 3.72 (broad multiplet, 1H. CH). 3.96 (sharp multiplet. 2H. CH2). 7.26–7.33 (aromatic H's). 7.83 (d. 1H. OH). 9.83 (m. 1H. HCl).

EXAMPLE 6 : ANTITETRABENAZINE TEST

Prevention on of tetrabenazine-induced sedation was measured using a modification of the method of Vernier et al., *First Hahnemann Symposium on Psychosomatic Medicine,* ed. Nodim and Moyer, pub Lea and Febiger, Philadelphia. 1962.

Mice, groups of 12 CD1 males each, were injected intraperitoneally (i.p.) with the hydrochloride salt of a compound of formula (I) in physiological saline solution or with physiological saline solution alone. Thirty minutes later each of the mice was injected (i.p.. 35 mg/kg) with a solution of tetrabenazine hydrochloride. Thirty minutes after the injection of tetrabenazine each mouse was examined for its level of exploratory behavior which was scored on a modification of the arbitrary scale defined by Vernier et al The result reported in Table I as the $ED_{50}$ value is the amount of the test compound required to reverse the tetrabenazine effects in 50 percent of the animals tested.

TABLE 1

| Antitetrabenazine Activity in the Mouse | |
| --- | --- |
| Compound | $ED_{50}$ (mg/kg i.p.) |
| Example 1 (HCl) | 2 |

TABLE 1-continued

| Antitetrabenazine Activity in the Mouse | |
| --- | --- |
| Compound | $ED_{50}$ (mg/kg i.p.) |
| Example 2 (HCl) | 5 |
| Example 3 (HCl) | 0.6 |
| Example 4 (HCl) | 3 |
| Example 5 (HCl) | 3 |

EXAMPLE 7: FORMULATIONS

A. Tablet

| Ingredient | Amount per Tablet |
| --- | --- |
| Compound of formula (I) (calculated as the base) | 50 mg |
| Lactose | 85 mg |
| Cornstarch | 50 mg |
| Micronized Silica Gel | 10 mg |
| Polyvinylpyrrolidone | 5 mg |

The lactose, cornstarch and compound of formula (I) are mixed together and granulated with a binder (polyvinylpyrrolidone in an alcoholic solution) to form granules.

The granules are passed through a 16–20 mesh screen, then air dried, lubricated with micronized silica gel and compressed into tablets. A film coat may then be applied if desired.

B. Capsule

| Ingredient | Amount per Capsule |
| --- | --- |
| Compound of formula (I) (calculated as the base) | 50 mg |
| Lactose | 125 mg |
| Cornstarch | 125 mg |

The above ingredients are mixed and filled into a two piece hard gelatin capsule.

C. Parenteral Solution

| | |
| --- | --- |
| Compound of formula (I) (as a pharmaceutically acceptable salt) | 25 mg (calculated as the base) |
| Sterile Water for Injections, q.s. to | 1.0 mL |

A pharmaceutically acceptable salt of a compound of formula (I) is dissolved in sterile water under sterile conditions to make 1.0 mL. Such a solution may be packaged in a sealed sterile ampoule to provide a unit dose or in a sterile vial for multiple doses. If the formulation is to be packed in a multi-dose container, the addition of a bacteriostat such as 0.2 to 0.5% w/v of phenol is desirable.

D. Suppository

The hydrochloride salt of a compound of formula (I) (50 mg, calculated as the base) is missed with 250 mg of softened or melted cocoa butter, and a suppository is formed by chilling and shaping in a mold.

We claim;

1. A (2S, 3S, 5R) compound of formula (I)

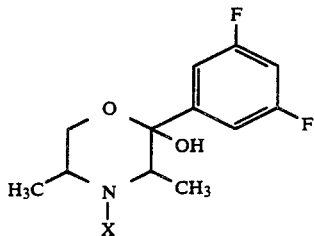

or the (+-)-(2R*,3R*,5S*) racemate thereof
wherein
X is hydrogen, alkyl of 1 to 6 carbon atoms, cycloalkyl of 3 to 6 carbon atoms or a group —CH$_2$—X$^1$ where X$^1$ is cycloalkyl of 3 to 6 carbon atoms,
or a pharmaceutically acceptable salt thereof.

2. A (2S,3S,5R) compound according to claim 1, or a pharmaceutically acceptable salt thereof, substantially free from the (2R,3R,5S) - enantiomorph.

3. A compound according to claim 1 or 2 wherein X is hydrogen or alkyl of 1 to 6 carbon atoms, or a pharmaceutically acceptable salt thereof.

4. (2S,3S,5R)-2-(3.5-Difluorophenyl)-3,5-dimethyl-2-morpholinol or a pharmaceutically acceptable salt thereof.

5. (+-)-(2R*,3R*,5S*)-2-(3,5-Difluorophenyl)-3,5-dimethyl-2-morpholinol or a pharmaceutically acceptable salt thereof.

6. (2S,3S,5R)-2-(3,5-Difluorophenyl)-3,4,5-trimethyl-2-morpholinol or a pharmaceutically acceptable salt thereof.

7. (+-)-(2R*,3R*5S*)-2-(3,5-Difluorophenyl-3,4,5-trimethyl-2-morpholinol or a pharmaceutically acceptable salt thereof.

8. (2S,3S,5R)-2-(3,5-Difluorophenyl)-4-ethyl-3,5-dimethyl-2-morpholinol or a pharmaceutically acceptable salt thereof.

9. A pharmaceutically acceptable salt of a compound according to claims 4, 5, 6, 7 or 8.

10. The hydrochloride salt of a compound according to claim 9.

11. A pharmaceutical composition comprising a (2S,3S,5R) compound of formula (I)

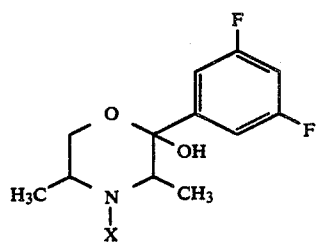

or the (+-)-(2R*,3R*,5S*) racemate thereof
wherein
X is hydrogen, alkyl of 1 to 6 carbon atoms, cycloalkyl of 3 to 6 carbon atoms or a group —CH$_2$—X$^1$ where X$^1$ is cycloalkyl of 3 to 6 carbon atoms.
or, a pharmaceutically acceptable salt thereof, together with a pharmaceutically acceptable carrier therefor.

12. A pharmaceutical composition according to claim 11 wherein the compound is selected from (2S,3S,5R)-2-(3,5-difluorophenyl)-3,5-dimethyl-2-morpholinol
(+-)-(2R*,3R*,5S*)-2-(3,5-difluorophenyl)-3,5-dimethyl-2-morpholinol (2S,3S,5R)-2-(3,5-difluorophenyl)-3,4,5-trimethyl-2-morpholinol
(+-)-(2R*,3R*,5S*)-2-(3,5-difluorophenyl)-3,4,5-trimethyl-2-morpholinol and
(2S,3S,5R)-2-(3,5-difluorophenyl)-4-ethyl-3,5-dimethyl-2-morpholinol.

13. A composition according to claim 12 for oral administration.

14. A composition according to claim 13 in the form of a capsule or tablet.

15. A method of treating narcolepsy-cataplexy syndrome in a human which comprises administering to said human an effective narcolepsy-cataplexy syndrome treatment amount of a compound of claim 1 or a pharmaceutically acceptable salt thereof.

16. A method of treating depression in a human identified as being depressed, which comprises administering to said human an effective antidepressant amount of a (2S, 3S, 5R) compound of formula (I)

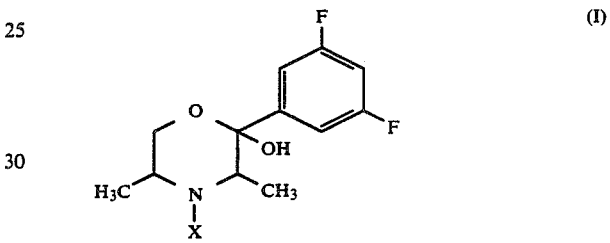

or the (+-)-(2R*,5S*) racemate thereof
wherein
X is hydrogen, alkyl of 1 to 6 carbon atoms, cycloalkyl of 3 to 6 carbon atoms or a group —CH$_2$X$^1$ where X$^1$ is cycloalkyl of 3 to 6 carbon atoms,
or a pharmaceutically acceptable salt thereof.

17. The method of claim 16, in which the compound (2S, 3S, 5R)-2-(3,5-Difluorophenyl)-3,5-dimethyl-2-morpholinol or a pharmaceutically acceptable salt thereof is administered.

18. The method of claim 16, in which a (2S, 3S, 5R) compound according to claim 1, or a pharmaceutically acceptable salt thereof, substantially from the (2S, 3S, 5R)-entantimorph is administered.

19. The method of claim 16 or claim 18, in which X is hydrogen or alkyl of 1 to 6 carbon atoms, or a pharmaceutically acceptable salt thereof is administered.

20. The method of claim 16, in which the compound (+-) -(2R*,3R*,5S*)-2-(3,5-Difluorophenyl)-3,5-dimethyl-2-morpholinol or a pharmaceutically acceptable salt is administered.

21. The method of claim 16, in which the compound (2S,3S,5R) -2-(3,5-Difluorophenyl)-3,4,5-trimethyl-2-morpholinol or a pharmaceutically acceptable salt is administered.

22. The method of claim 16, in which the compound (+-) -(2R*,3R*,5S*)-2-(3,5-Difluorophenyl)-3,4,5-trimethyl-2-morpholinol or a pharmaceutically acceptable salt is administered.

23. The method of claim 16, in which the compound (2S,3S,5R) -2-(3,5-Difluorophenyl)-4-ethyl-3,5-dimethyl-2-morpholinol or a pharmaceutically acceptable salt is administered.

24. A method of treating a human identified as being depressed, comprising administering to said human a pharmaceutically acceptable salt of (2S,3S,5R)-2-(3,5-Difluorophenyl)-3,5-dimethyl-2-morpholinol.

25. The method of claim 24, in which the hydrochloride salt is administered.

26. The method of claim 24 or claim 25, in which the salt is administered orally or parenterally.

27. A pharmaceutically acceptable salt of (2S,3S,5R)-2-(3,5-Difluorophenyl)-3,4,5-trimethyl-2-morpholinol.

28. The hydrochloride salt of (2S,3S,5R)-2-(3,5-Difluorophenyl)-3,4,5-trimethyl-2-morpholinol.

29. A method of treating depression in a human identified as being depressed, which comprises administering to said human an effective antidepressant amount of the salt of claim 19 or 20.

30. A method of treating narcolepsy—cataplexy syndrome in a human identified as being depressed, which comprises administering to said human an effective narcolepsy— cataplexy syndrome treatment amount of a compound of claim 19 or 20.

31. A tablet or capsule containing the salt of claim 19 or 20.

32. The method of claim 21, in which the salt is administered orally.

33. The method of claim 22, in which the salt is administered orally.

* * * * *